United States Patent

Heidmueller

[11] Patent Number: 5,330,436
[45] Date of Patent: Jul. 19, 1994

[54] INTRODUCING DEVICE

[76] Inventor: Harald Heidmueller, Heidenrichstrasse 10, 5000 Koeln 80, Fed. Rep. of Germany

[21] Appl. No.: 66,201

[22] Filed: May 25, 1993

[30] Foreign Application Priority Data

May 26, 1992 [DE] Fed. Rep. of Germany ....... 4217324

[51] Int. Cl.$^5$ .............................................. A61B 17/34
[52] U.S. Cl. .................................. 604/167; 604/264; 604/174; 606/185
[58] Field of Search ................ 606/185; 604/167, 169, 604/164, 264, 174, 256, 249

[56] References Cited

U.S. PATENT DOCUMENTS

| 4,112,932 | 9/1978 | Chiulli | 604/264 X |
| 4,535,773 | 8/1985 | Yoon | 128/630 X |
| 5,112,321 | 5/1992 | Hiltebrandt | 604/167 X |
| 5,217,441 | 6/1993 | Shichman | 606/185 X |
| 5,224,930 | 7/1993 | Spaeth et al. | 606/185 X |

FOREIGN PATENT DOCUMENTS

| 433581 | 6/1991 | European Pat. Off. | 604/264 |
| 92/14414 | 2/1992 | European Pat. Off. | |
| 4002235 | 1/1990 | Fed. Rep. of Germany | |

Primary Examiner—Michael H. Thaler
Attorney, Agent, or Firm—Diller, Ramik & Wight

[57] ABSTRACT

An introducing device serves to introduce instruments into a living body. A trocar pipe is fastened to a housing. The housing contains two axially aligned channels between which a sealing slide is arranged. The slide has a passage opening that may be aligned with the channels in order to pass an instrument of corresponding diameter therethrough. In the slide, an auxiliary slide is provided that has a passage opening of smaller diameter. When the auxiliary slide is advanced in the slide, its passage opening gets into the area of the passage opening of the slide and reduces the same. Thus, the diameter of the passage opening can be adapted to that of the instrument used so that the location of passage is sealed.

9 Claims, 4 Drawing Sheets

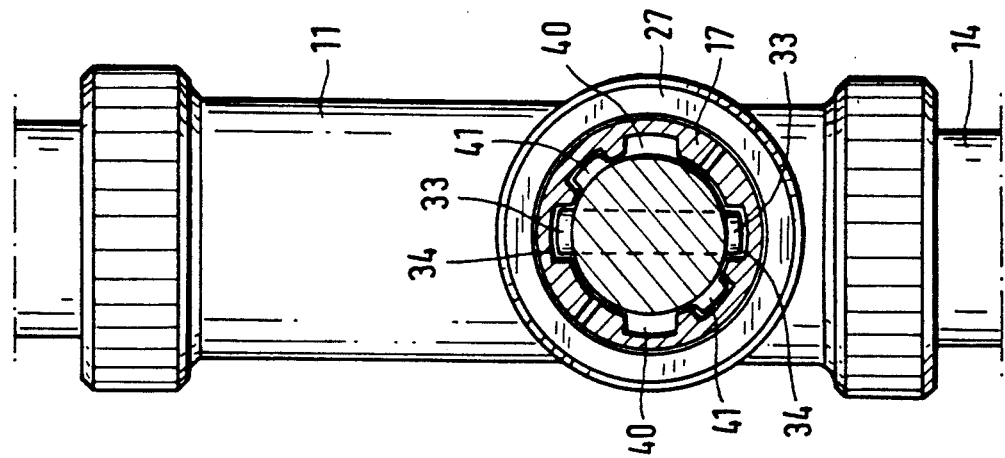
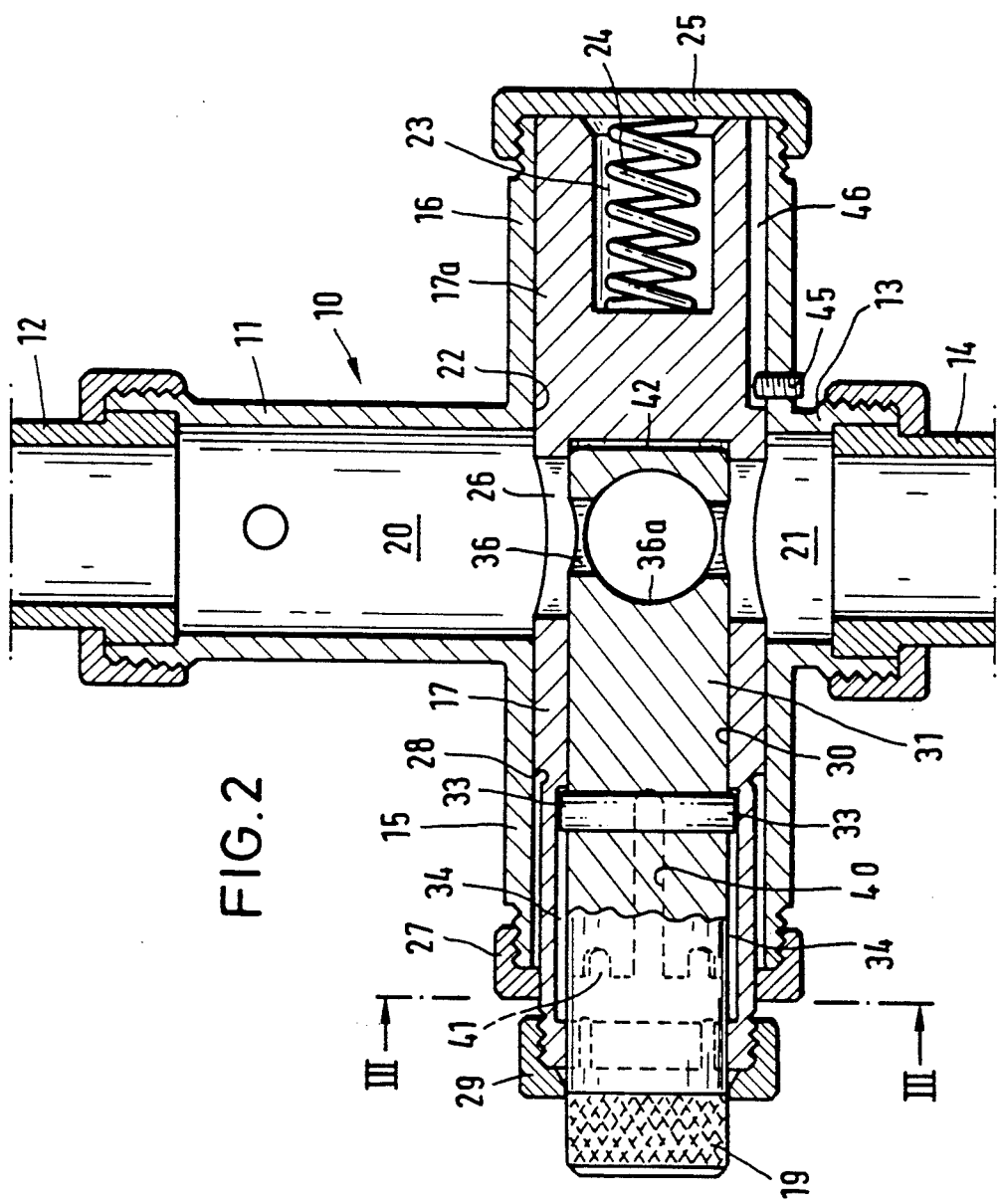

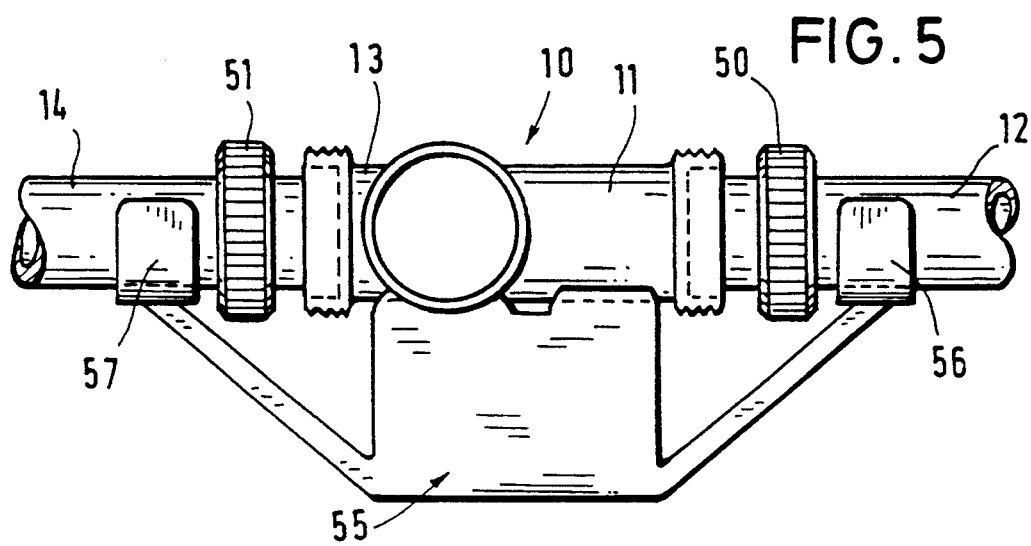
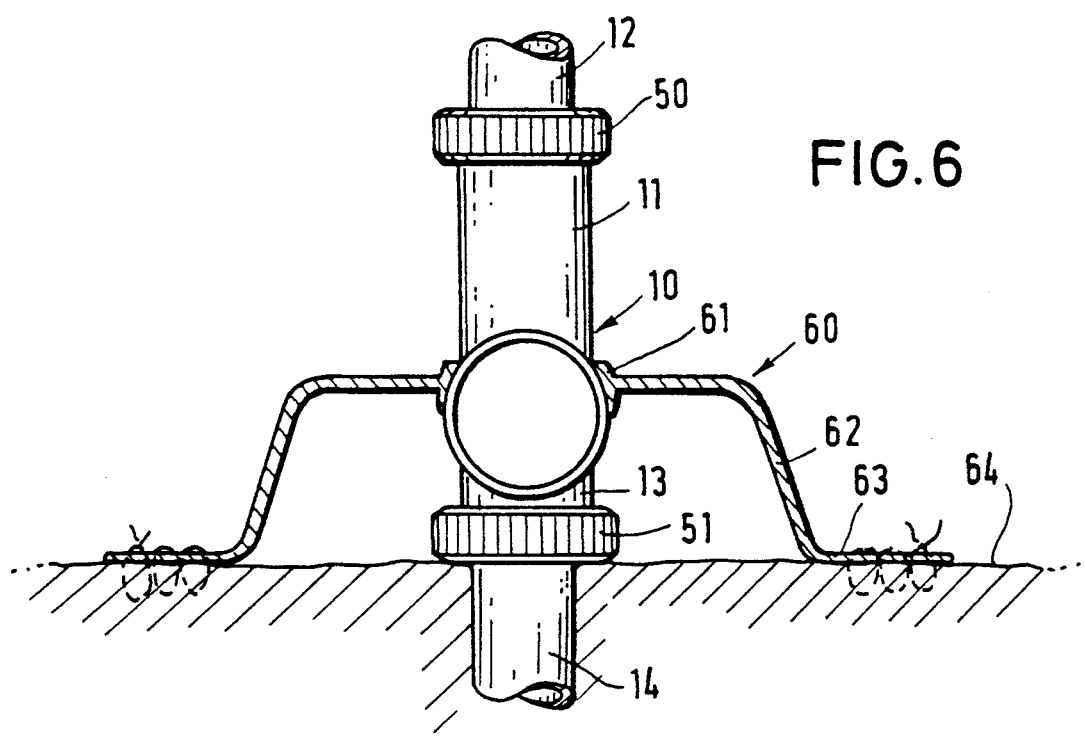

INTRODUCING DEVICE

BACKGROUND OF THE INVENTION

The invention refers to an introducing device for inserting instruments, for example, laparascopic and laparatomic instruments, into a living body.

From German Patent 40 02 235, an introducing device is known for the percutaneous introduction of an endoscope. A housing includes a slide having an opening adapted to be made flush with a channel through which a trocar is passed. The body is punctured with the trocar projecting from the trocar pipe, whereafter the introduction device is pushed up to the housing. Then, the trocar is removed and gas is simultaneously introduced into the body through the trocar pipe. After the withdrawal of the trocar, a spring means pushes the slide is pushed into the closed position in which it closes the channel. Thereby, the channel is sealed from the environment. For a later insertion of an instrument through the housing and the trocar pipe into the body, the closing slide is manually moved into the opened position.

Instruments for insertion into the body via a trocar pipe may differ in diameter. In order to maintain the sealing, it is presently required to set reducing sleeves into the trocar pipe, which is troublesome and time consuming.

From U.S. Pat. No. 4,112,932, an introducing device with a trocar pipe is known, having two discs as a housing that are rotatable relative to each other about a common axis. The disc adjacent the trocar pipe has an opening and the other disc is provided with a ring of passage openings of equal size. Nozzles of equal diameter that are closed by rubber caps, respectively, branch from the passage openings. Each rubber cap is formed with a hole. For the adaptation to the size of an instrument to be used, a rubber cap with a matching hole size has to be selected. This device is complicated to handle. Since there is no closed housing, problems with sterility arise.

Patent Application WO 92/14414 describes an introducing device wherein an adjusting member is rotatably or slidably arranged within a housing and has a plurality of passage openings of different diameters that are selectively adjustable with respect to the openings of the housing for the sealed passage of an instrument. Thus, a passage opening of fitting size may be selected for every trocar or instrument, yet a larger number of passage openings of different sizes require very complex slide structures that are hard to realize.

It is an object of the present invention to provide an introducing device that is simple to handle and allows for a fast adaptation to instruments of different cross-sectional size.

SUMMARY OF THE INVENTION

Besides a slide, the passage opening of which may be aligned with the channels, the introducing device of the present invention also comprises an auxiliary slide having a passage opening smaller than that of the slide.

The auxiliary slide may be moved relative to the slide such that its passage opening is flush with that of the slide so that the auxiliary slide reduces the size of the passage opening of the slide. Thus, at least two passage openings of different size can be realized. Preferably, a spring urges the slide into a position in which it separates the channels from each other. In order to align the passage opening with the channels, the slide is moved. The movement of the slide is always the same, regardless of the size of the respective required passage opening. The auxiliary slide provided at the slide can reduce the available passage opening, however, only the slide must be moved before the insertion of a trocar or an instrument, and this actuation of the slide is always done in the same manner. Thus, the handling of the instrument is facilitated.

The auxiliary slide is adjustably provided at the slide and may be moved together with the same. The adjustment of the auxiliary slide—and thus the determination of the size of the passage opening—is performed prior to the insertion. In the introduction process only the slide is displaced such that the respective effective passage opening is aligned with the channels. To this avail, the slide is normally pushed into the housing up to an end abutment. This results in the reduction of the risk of setting or selecting a wrong passage opening. Besides an axial displaceability of the slide and an axial displaceability of the auxiliary slide relative to the slide, the auxiliary slide and/or the slide may further be rotatable about their longitudinal axis so as to align different passage openings with the channels of the housing.

BRIEF DESCRIPTION OF THE DRAWINGS

The following is a detailed description of an embodiment of the present invention taken in conjunction with the accompanying drawings.

In the Figures:

FIG. 2 is a longitudinal section of the introducing device of FIG. 1,

FIG. 3 is a section along line III—III in FIG. 2,

FIG. 5 is a view of a bracket for facilitating the mounting of the pipes, and FIG. 6 is a section of a fixing means with which the introducing device may be connected.

DESCRIPTION OF THE PREFERRED EMBODIMENT

Figure 1:
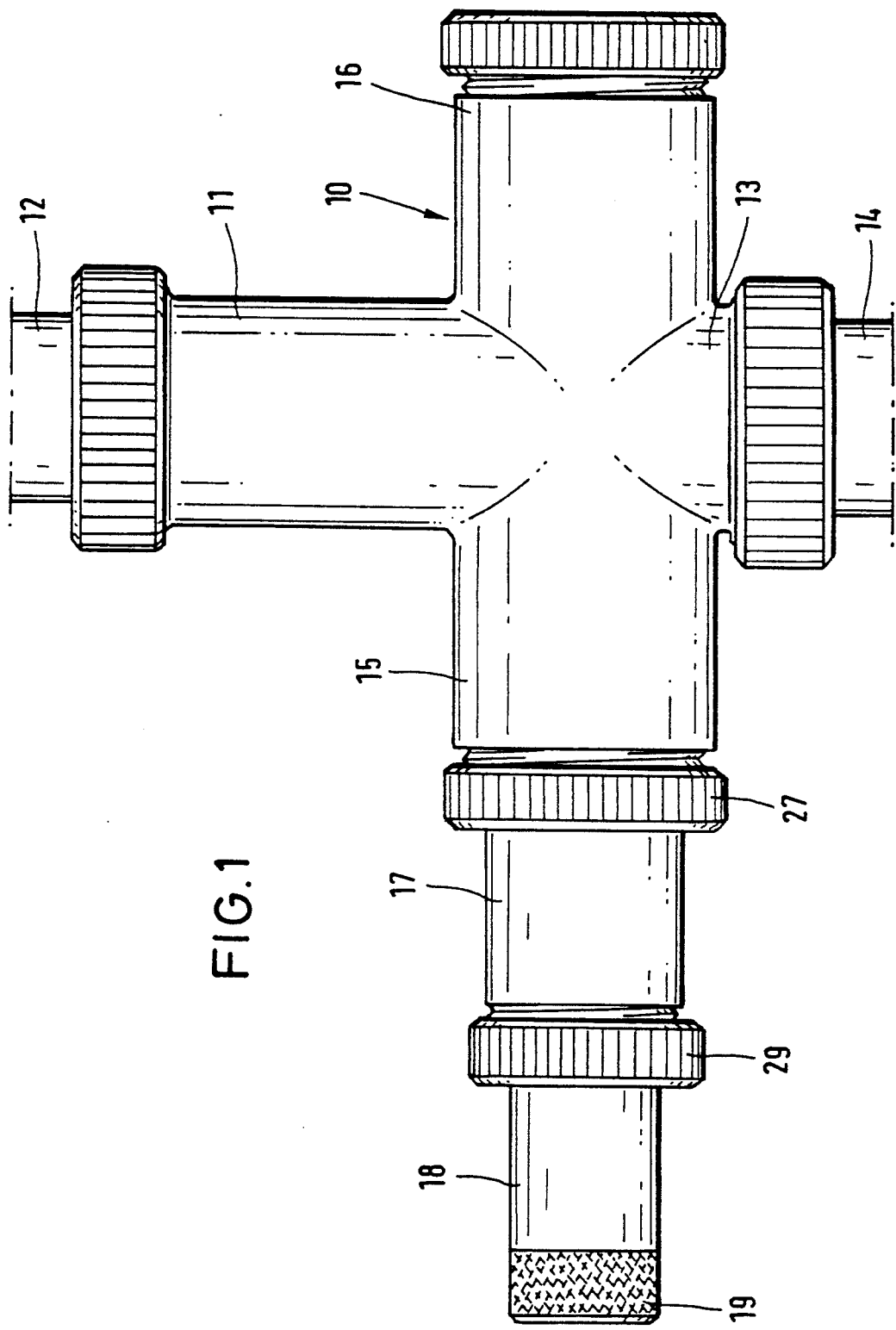
FIG. 1 is an illustration of the introducing device.

Referring to FIG. 1, the introducing device has a cross-shaped housing 10, the arms of which are formed by tubular connection pieces. The tubular connection piece 11 serves for the connection of a pipe 12 through which an instrument (not illustrated) may be advanced. The tubular connection piece 13 opposite the tubular connection piece 11 serves for the connection of a trocar pipe 14. The two tubular connection pieces 15 and 16 extending therefrom in opposite directions, form a guiding channel for a slide 17 in which an auxiliary slide 18 is provided for displacement. The auxiliary slide 18 extends from the end of the slide 17 and has a handle 19 provided at its end.

Referring to FIG. 2, the tubular connection pieces 11 and 13 each comprise a channel 20, 21. These channels 20 and 21 are in coaxial alignment. The guiding channel 22 for the slide 17 extends rectangularly to the channels 20, 21. Within the guide channel 22, the slide 17 is displaceable in the longitudinal direction of the guiding channel. The slide 17 fills the diameter of the guiding channel 22 completely so that it seals the guiding channel. At the end of the slide 17 that protrudes into the tubular connection pipe 16, a recess 23 is provided in which a spring device 24 is arranged that abuts against a screw lid 25 closing the tubular connection piece 16 and urges the slide 17 to the left, as illustrated in FIG. 2. FIG. 2 shows the spring device 24 in the compressed (tensioned) state. In this state, in which the slide 17 abuts against the screw lid 25, a transversally extending passage opening 26 provided in the slide 17 is in axial alignment with the channels 20 and 21. An instrument advanced through the tubular connection piece 11 to the tubular connection piece 13 can pass through the passage opening 26. This instrument has a diameter corresponding to the diameter of the passage opening 26 so that is closes the passage opening in a sealing manner. When the instrument is withdrawn from the housing 10, the spring device 24 relaxes and urges the sealing portion 17a into the area of the channels 20 and 21 which are thereby separated from each other.

The end of the slide 17 projects from the tubular connection piece 15. A screw cap 27 is mounted on the end of the tubular connection piece 15, which limits the outwardly directed movement of the slide 17 by having an annular shoulder 28 of the slide 17 abut thereagainst. The slide 17 extends through a central opening of the screw cap 27. Its end is provided with a thread onto which a tightening nut is screwed that may be tightened in order to urge the end of the slide 17 radially inward.

A dead bore 30 extends in the slide 17, in which the auxiliary slide 31 may be displaced linearly. The auxiliary slide 31 has two lugs. 33 protruding to opposite sides, which immerse in longitudinally extending grooves 34 of the dead bore 30, thereby preventing a turning of the auxiliary slide 31 with respect to the slide 17. The outer end of the auxiliary slide 31 extends through an opening in the tensioning nut 29. When the tensioning nut 29 is tightened, it presses the longitudinally extending tensioning slits at the end of the slide 17 together, whereby the wall of the slide 17 is pressed radially against the auxiliary slide 31 and both slides are chucked relative to each other. The tensioning nut 29 forms a releasable holding means with which the auxiliary slide 31 may be chucked in the slide 17 and with which it may be fixed relative to the slide. Such fixing is done at each of the two end positions of the auxiliary slide 31, one of which is depicted in FIG. 2 an the other one being illustrated in FIG. 4. In each of these end positions, the pins 33 abut against an abutment of the groove 34 or the tensioning nut 29.

Near its end, the auxiliary slide 31 has a passage opening 36 of a diameter smaller than the passage opening 26 of the slide. The passage opening 36 is arranged axially parallel to the passage opening 26, and in the advanced position of the auxiliary slide 31 it is in coaxial alignment with the passage opening 26. In this position, as illustrated in FIG. 2, the smaller passage opening 36 determines the size of the overall passage opening.

The auxiliary slide 31 has a further transversal passage opening 36a arranged under an angle of, e.g., 90° to the passage opening 36 and on the same transversal plane as the passage opening 36, the diameter of the passage opening 36a being smaller than that of the passage opening 26, yet different from that of the passage opening 36. By turning the auxiliary slide 31 about its longitudinal axis, the passage opening 36a may be aligned with the passage opening 26.

Referring now to FIG. 3, when the pins 33 project into the grooves 34, the passage opening 36 is in alignment with the passage opening 26. Further grooves 40 are offset by 90° with respect to the grooves 34. When the pins 33 are within the grooves 40, the passage opening 36a is in axial alignment with the passage opening 26. The slide 17 is provided with further grooves 41 offset by 45° with respect to the grooves 34 and 40. These grooves 41 are much shorter than the grooves 34 and 40. When the pins 33 are inserted into the shorter grooves 41, the auxiliary slide 31 cannot be advanced along the slide far enough for its end face 42 to reach the region of the passage opening 26 of the slide 17. This is the inactive position of the auxiliary slide 31, in which only the passage opening 26 of the slide 17 determines the diameter of the overall passage opening.

As a twisting contrivance for the slide 17, an inwardly projecting pin 45 that immerses into a longitudinal groove of the slide 17 is provided in the tubular connection piece 16.

FIG. 2 illustrates the state in which the pins 33 immerse into the grooves 34, whereby the passage opening 36 is aligned with the passage opening 26. The auxiliary slide 31 is in its front end position in the slide 17. By pressing against the handle 19, the slide 17 has been advanced up to against its end abutment, i.e., the screw heads 25. In this position, an elongate instrument may be pushed through the passage opening 36. After the withdrawal of the instrument, the spring device 24 urges the slide 17, together with the auxiliary slide 31, into the end position in which the sealing portion 17a separates and seals the channels 20 and 21 from each other.

Figure 4:
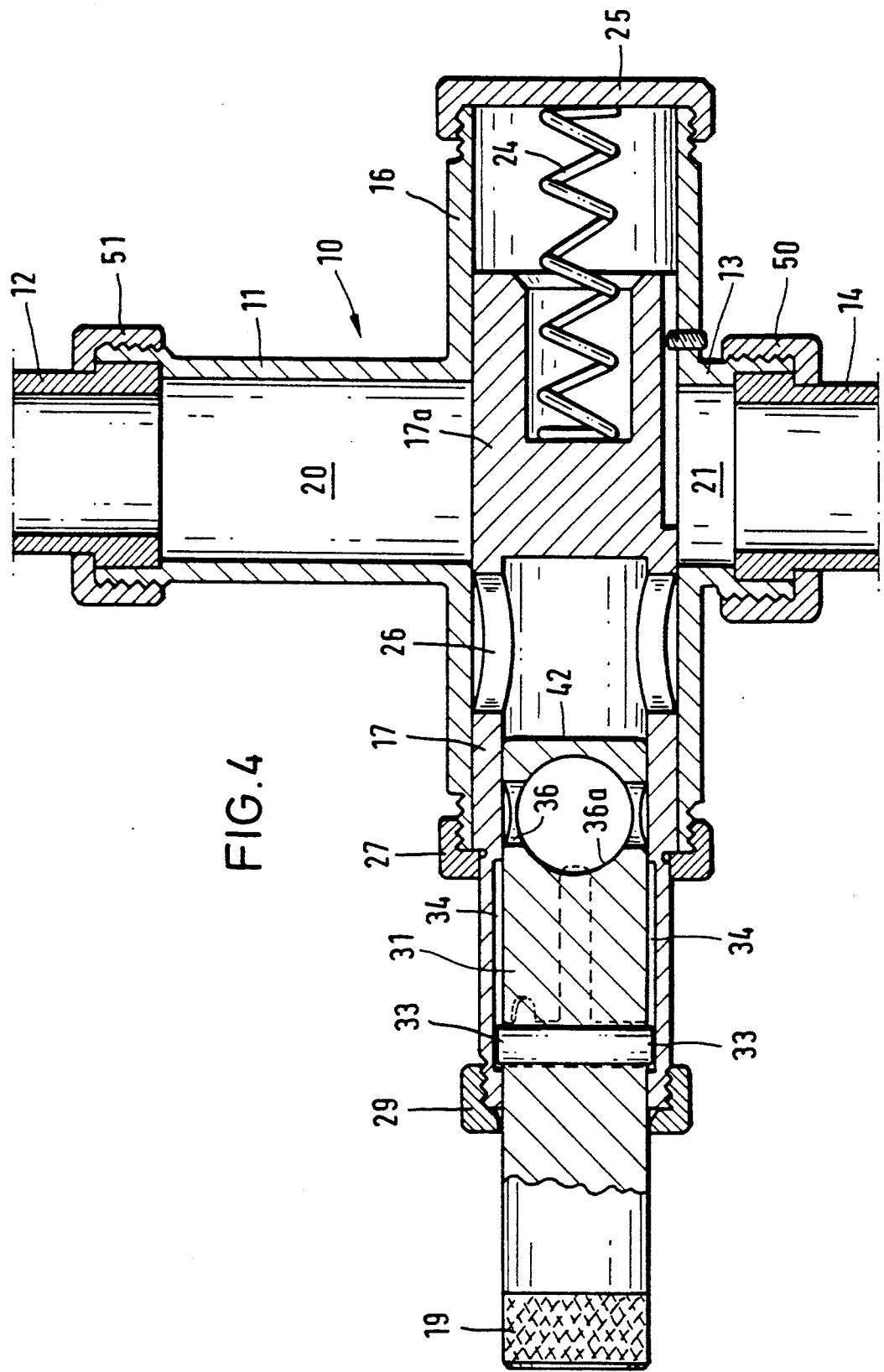
FIG. 4 is a view similar to FIG. 2, illustrating the rest position of the slide with the auxiliary slide in the inactive position.

Referring to FIG. 4, the auxiliary slide 31 is depicted in its rear end position in which it may be rotated about its axis in order to selectively introduce the pins 33 into one of the grooves 34, 40 or 41, as illustrated in FIG. 3. If the pins 33 are introduced into the grooves 40, the passage opening 36a is in axially parallel alignment with the channels 20 and 21. When the handle 19 is pushed forward, the passage opening 36a attains axial alignment with the passage opening 26 of the slide 17 and, upon further advancing the auxiliary slide 31, the slide 17 is brought into a position in which the passage openings 36 and 36a get into axial alignment with the channels 20 and 21. If the pins 33 of the auxiliary slide 31 (with the tensioning nut 29 loosened) is inserted into the grooves 41 and if the auxiliary slide 31 is advanced thereafter, the end face 42 will not reach the region of the passage opening 26. Upon further advancing the auxiliary slide, the passage opening 26 gets into axial alignment with the channels 20 and 21 so that it alone determines the diameter of the overall passage opening. The guiding channel 30 for the auxiliary slide 31 extends over the region of the passage opening 26 so that this passage opening is formed in two opposite wall portions of the tubular cylindrical slide 17.

The housing 10, as well as the slide 17 and the auxiliary slide 31 may be formed as plastics parts that fit into one another with little play and in a sealing manner.

The pipe 12 and the trocar pipe 14 are fastened to the housing 10 by means of swivel nuts 50 and 51 that surround the respective pipe and are screwed onto an outer thread of the respective tubular piece 11 or 13 of the housing 10. In order to facilitate the mounting of the pipes 12 and 14 to the housing 10, a bracket 55, as illustrated in FIG. 5, is used which has clamping holders 56 and 57 for each of the pipes 12 and 14 and bridges the tubular connection pieces 11 and 13 of the housing 10. The pipes 12 and 14 are set into the holders 56 and 57. The bracket 55 is designed such that, in this state, the pipes lie in front of the respective tubular connection piece 11 or 13. The bracket 55 is fastened to the housing 10 by means of a suitable clamping holder. Thereafter, only the swivel nuts 50 and 51 surrounding the pipes 12 and 14 have to be screwed tight. The bracket 55 facilitates the aligning of the pipes with the housing 10 and the fastening of these pipes at the housing.

FIG. 6 illustrates a fixing device 60 with a ring 61 that may be clamped at the housing 10 and from which a plate-shaped holding device 62 branches that encloses the tubular connection piece 13. The outer edge of the holding device 62 is formed as a flange 63 laid against the skin 64 of a patient if the trocar pipe 14 protrudes into the patient's body. The flange 63 serves in suturing the fixing device 60 to the patient's skin. The fixing device 60 firmly holds the housing 10 of the introducing device on the patient's body. The fixing device 60 allows for the use of the introducing device as a dwell-in device for introducing instruments into the patient's body, for example, for follow-up examinations. The bedridden patient can carry the introducing device with the trocar pipe 14 for several days, for example. Follow-up examinations or posterior operations may then be performed at any time without stressing the patient by additional punctures.

We claim:

1. An introducing device for introducing instruments into a body comprising a trocar pipe (14), a housing (10) with two coaxially aligned oppositely directed channels (20, 21), at least one of said channels (20, 21) is connected with said trocar pipe (14) and between which a slide (17) is arranged that is linearly movable along an axis and transverse to said channels (20, 21), said slide (17) having a first passage opening 926) alignable with said channels (20, 21), said slide (17) is coupled with an auxiliary slide (31) movable in the direction of said axis and having a second passage opening (36) of smaller dimension then that of said first passage opening (26), and said auxiliary slide (31) is adjustable with respect to said slide (17) such that said first passage opening (26) and said second passage opening (36) come into axial alignment with each other.

2. The introducing device according to claim 1, wherein said auxiliary slide (31) serves as a handle for advancing said slide (17), and an engaging device (33) of said auxiliary sleeve (31) selectively engages engaging devices (34, 40) of said slide (17) in a first position at which said first and second passage openings (26, 36, respectively) are generally axially aligned (FIG. 2) and in a second position at which said first and second passage openings (26, 36, respectively) are not axially aligned (FIG. 4).

3. The introducing device according to claim 1, wherein said auxiliary slide (31) is movable within said slide (17).

4. The introducing device according to claim 1, wherein said auxiliary slide (31) has two or more second passage openings (36a) of different sizes that may be aligned towards said channels (20, 21) by turning said auxiliary slide (31).

5. The introducing device according to claim 1, wherein said auxiliary slide (31) has two or more circumferentially distributed first passage openings (36, 36a) of different sizes that may be aligned with said channels (20, 21) by turning said slide (17) about its axis.

6. The introducing device according to claim 1, wherein said housing (10) is of cross-shaped structure, two oppositely directed arms (11, 13) containing said channels (20, 21), one arm (15) containing said slide (17) and said auxiliary slide (31) and another arm (16) contains a sliding space for the immersion of said slide (17).

7. The introducing device according to claim 1, wherein a spring device (24) urges said slide (17) into a closed position in which it blocks said channels (20, 21).

8. The introducing device according to claim 1 including a fixing device (60) mounted to said housing (10) for fixing said housing (10) to a patient's body.

9. An introducing device for introducing instruments into a body comprising a trocar pipe (14), a housing (10) with two coaxially aligned oppositely directed channels (20, 21), at least one of said channels (20, 21) is connected with said trocar pipe (14) and between which a slide (17) is arranged that is linearly movable along an axis and transversal to said channels (20, 21), said slide (17) having a first passage opening (26) alignable with said channels (20, 21), bracket means (55) for mounting to said housing (10) having holding means (56, 57) for holding said trocar pipe (14) and a further pipe (12) in alignment with said channels (20, 21), and said trocar pipe (14) and said further pipe (12) are fastened to said housing (10) by means of swivel nuts (51).

* * * * *